(12) United States Patent
Thanavala et al.

(10) Patent No.: US 6,537,265 B2
(45) Date of Patent: Mar. 25, 2003

(54) METHOD FOR NASAL APPLICATION OF A MEDICINAL SUBSTANCE

(75) Inventors: Yasmin Thanavala, Williamsville, NY (US); Anju Visweswaraiah, Delmar, NY (US); Lauren O. Bakaletz, Hilliard, OH (US); Laura Anne Novotny, Delaware, OH (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 09/991,835

(22) Filed: Nov. 5, 2001

(65) Prior Publication Data

US 2002/0198510 A1 Dec. 26, 2002

Related U.S. Application Data

(63) Continuation-in-part of application No. 09/877,605, filed on Jun. 8, 2001, now abandoned.

(51) Int. Cl.$^7$ .......................... A61M 31/00; A61B 19/00
(52) U.S. Cl. ........................ 604/514; 128/898
(58) Field of Search ............................. 600/500, 514, 600/516, 94.01; 128/200.14, 898; 424/434

(56) References Cited

U.S. PATENT DOCUMENTS

| | | | | |
|---|---|---|---|---|
| 598,286 A | * | 2/1898 | Curran | |
| 4,381,773 A | * | 5/1983 | Goodnow et al. | 128/200.14 |
| 4,886,493 A | * | 12/1989 | Yee | 604/54 |
| 5,116,311 A | * | 5/1992 | Lofstedt | 604/54 |
| 5,284,132 A | * | 2/1994 | Geier | 128/200.22 |
| 5,429,600 A | * | 7/1995 | Heinke | 604/54 |
| 5,713,855 A | * | 2/1998 | Shippert | 604/54 |
| 6,085,753 A | * | 7/2000 | Gonda et al. | 128/898 |

OTHER PUBLICATIONS

Berstad, Aud Katrine Herland, et al. "Inactivated Meningococci and Pertussis Bacteria are Immunogenic and Act as Mucosal Adjuvants for a Nasal Inactivated Influenza", Vaccine, 182000, pp. 1910–1919.

Childers, Noel K., et al. "Adjuvant activity of Monophosphoryl Lipid A for Nasal and Oral Immunization with Soluble of Liposome–Associated Antigen", Infection and Immunity,2000, pp. 5509–5516.

Dupuy, Catherine, et al. "Nasal Immunization of Mice with Human Papillomavirus Type 16 (HPV–16) Virus–Like Particles or with HPV–16 L1 Gene Elicits Specific Cytotoxic T Lymphocytes in Vaginal Draining Lymph Nodes", Journal of Virology, 1999, pp. 9063–9071.

Eyles, Jim E., et al. "Immunological Responses to Nasal Delivery of Free and Encapsulated Tetanus Toxoid: Studies on the Effect of Vehicle Volume", International Journal of Pharmaceutics,189, 1999, pp. 75–79.

Gallichan, W. Scott, et al. "Long–Term Immunity and Protection Against Herpes Simplex Virus Type 2 in the Murine Female Genital Tract after Mucosal but not Systemic Immunization",Journal of Infectious Diseases, 177, 1998, pp. 1155–1161.

Klavinskis, Linda S., et al. "Intranasal Immunization with Plasmid DNA–Lipid Complexes Elicits Mucosal Immunity in the Female Genital and Rectal Tracts", Journal of Immunology,1999, pp. 254–262.

Lundholm, Peter, et al. "Induction of Mucosal IgA by a Novel Jet Delivery Technique for HIV–1 DNA", Vaccine, 17, 1999, pp. 2036–2042.

McCluskie, Michael J., et al. "Cutting Edge: CpG DNA is a Potent Enhancer of Systemic and Muscosal Immune Responses Against Hepatitis B Surface Antigen with Intranasal Administration to Mice", Journal of Immunology, 1998, pp. 4463–4466.

Pickett, Thames E., et al. "In Vivo Characterization of the Murine Intranasal Model for Assessing the Immunogenicity of Attenuated *Salmonella enterica* Serovar Typhi Strains as Live Mucosal Vaccines and as Live Vectors", Infection and Immunity, vol. 68, No. 1, 2000, pp. 205–213.

Saunders, Nancy B., et al. "Immunogenicity of Intranasally Administered Meningococcal Native Outer Membrane Vesicles in Mice", Infection and Immunity, vol. 67, No. 1, 1999, pp. 113–119.

Shen, Xuzhuang, et al. "Group B Streptococcus Capsular Polysaccharide–Cholera Toxin B Subunit Conjugate Vaccines Prepared by Different Methods for Intranasal Immunization", Infection and Immunity, vol. 69, No. 1, 2001, pp. 297–306.

Shen, Xuzhuang, et al. "Systemic and Mucosal Immune Responses in Mice after Mucosal Immunization with Group B Streptococcus Type III Capsular Polysaccharide–Cholera Toxin B Subunit Conjugate Vaccine", Infection and Immunity, vol. 68, No. 10, 2000, pp. 5749–5755.

Trolle, Sylvine, et al. "Intranasal Immunization with Protein–Linked Phosphorycholine Protects Mice Against a Lethal Intranasal Challenge with *Streptococcus pneumoniae*", Vaccine, 18,2000, pp. 2991–2998.

* cited by examiner

*Primary Examiner*—Sharon Kennedy
(74) *Attorney, Agent, or Firm*—Michael L. Dunn

(57) ABSTRACT

A method for nasal application of a medicinal substance by applying the substance through the nose in a maximum amount that is insufficient to stimulate an excretory response that would clear a significant portion of the substance from nasal and sinus passages. Within a time period of less than one hour, the application of the substance through the nose in an amount that is insufficient to stimulate an excretory response that would clear a significant portion of the substance from nasal and sinus passages is repeated. The repeated application, at a minimum, is done a sufficient number of times to provide an effective total dose of the substance. The repeated application, in any case, is done at least once.

14 Claims, No Drawings

METHOD FOR NASAL APPLICATION OF A MEDICINAL SUBSTANCE

This invention was made with funding from the National Institute of Health Grant Number NIH IPOI A1 46422-01A1. The United States Government may have certain rights in this invention.

BACKGROUND OF THE INVENTION

This is a Continuation-in-Part of U.S. application Ser. No. 09/877,605, filed Jun. 8, 2001, now abandoned.

This invention relates to delivery of a medical substance to a mammal and more particularly relates to nasal delivery of such a substance for absorption, reaction or other utilization.

Nasal administration of medical substances has had significant disadvantages. Dosages have been difficult to control due to excretory responses to administration, e.g. sneezing and mucosal excretion that removes or significantly reduces the substance from the nasal passages and sinuses. Another problem is that administered substances removed by an excretory response are often swallowed leading to nausea, stomach upset or other digestive disturbance. An even more serious problem is that if the excretory response is strong enough, the substance can be inhaled causing coughing or more serious pulmonary distress. An even further problem is that when a significant amount of the medical substance is removed by an excretory response, the material excreted is wasted material, thus increasing costs and inefficiencies associated with nasal administration.

BRIEF DESCRIPTION OF THE INVENTION

In accordance with the invention a method is therefore provided for nasal application of a medicinal substance which overcomes the above disadvantages. In particular, the method comprises applying the substance through the nose in a maximum amount that is insufficient to stimulate an excretory response that would clear a significant portion of the substance from nasal and sinus passages and within a time period of less than one hour, and repeating the application of the substance, through the nose in an amount that is insufficient to stimulate an excretory response that would clear a significant portion of the substance from nasal and sinus passages. The repeated application, at a minimum, is done a sufficient number of times to provide an effective total dose of the substance. The repeated application, in any case, is done at least once.

DETAILED DESCRIPTION OF THE INVENTION

"Nasal application", as used herein, means applied through the nose into the nasal or sinus passages or both. The application may, for example, be done by drops, sprays, mists, coatings or mixtures thereof applied to the nasal and sinus passages.

"Medicinal substance" means any substance capable of being effectively applied nasally. Such substance are usually in the form of liquids, but may also be vapors or fine solids. Such substances are either absorbed by the tissues and vessels in the nasal and sinus passages (nasally absorbable) or interact with the surface of such passages (nasally active). Such substances may for example include vaccines, antigens, epitopes, adjuvants, viral vectors, bacterial vectors, immune modulators, delivery vehicles, and other drugs such as antibiotics, antivirals, hormones, antibodies, anti-inflammatories, antipyretics, antispasmotics, sedatives, anesthetics, chemotherapeutic agents, analgesics, vasodialators, and vasoconstrictors.

When the medical substance is a vaccine it may for example be a vaccine for non-typeable *haemophilus influenzae* which may contain an epitope of P5, P6 or both P5 and P6 proteins of *haemophilus influenzae*. The vaccine may also for example be a vaccine against hepatitis B.

The maximum amount that is insufficient to stimulate an excretory response that would clear a significant portion of the medicinal substance from the nasal and sinus passages is readily determined by observation and varies with the substance being applied, the surface area of the nasal passages and sinuses and with the size and species of animal. In the case of a mouse, the maximum amount is usually between about 2 and 10 $\mu l$ and for a human is usually from about one to about three drops.

"Excretory response" means a response by the animal that tends to clear a significant portion of the medicinal substance from the nasal passages and sinuses. Such responses include increased secretions from the surfaces of the nasal passages and sinuses, and sneezing. Increased secretions may dilute the substance and can be removed from the nasal passages and sinuses by sneezing, blowing, dripping, coughing and swallowing.

"Significant portion" means that the effectiveness of the substance is substantially reduced (e.g. a reduction in effectiveness greater than 20 percent) due to excretion. A "significant portion" would normally be between 10 and 30 percent of the applied dose.

Repeated applications to obtain a maximum dose without stimulating an excretory response, for practical reasons related to the value of doctor and patient time, are usually completed within an hour and preferably less, e.g. one-half hour. The total number of doses within an hour is at least two but to obtain maximum effective dose, usually the number of doses is between 3 and about 20 and preferably between 4 and about 12 within an hour. Commonly, the number of applications is from 3 to about 15 applications within an hour. The time interval between doses is usually between about 30 seconds and about 15 minutes.

The method of the invention is applicable to essentially any mammal having easily accessible nasal passages and sinuses, e.g. mice, rats, chinchillas and other rodents, cats, monkeys, apes and humans. It has been found that position of certain mammals may increase effectiveness. For example, application is more effective in a prone chinchilla than a supine chinchilla and more effective in a supine mouse than a prone mouse. Nevertheless, the method of the invention using repeated doses, below the amount that stimulates a significant excretory response, is more effective than single doses when other variables are constant.

The following examples serve to illustrate but not limit the invention.

To show the distribution of liquid administered through the nose, Evans Blue Dye (0.3%) was administered through a micropipette tip into the nose of mice and chinchillas at various doses, at various levels of sedation or anesthesia, and with the animals in various positions.

The results clearly show that when a lower dose is used, more dye is retained in the nasal passages and sinuses and less dye is lost to the esophagus, stomach, intestines and lungs. The results further clearly show that when a series of low doses are used near the point at which the animal excretes the dye to the esophagus, stomach and intestines, more material can be retained in the nasal passages and sinus cavities than when a single larger dose is used. Further interesting results are that more dye is retained in the nasal passages and sinuses in the chinchilla, when the dye is administered in the prone position than when administered in the supine position but the converse is true for mice. Further, more dye is retained in the nasal passages and sinuses when administered to an alert chinchilla but again the converse is true for the mouse where an anesthetized state is preferred. In most cases, a divided dose permits more material to be retained in the nasal area.

The following table shows results for tests conducted with mice. Except as noted above, similar results occurred with tests conducted using chinchillas.

In the following tables "−" means that no dye is present, "traces" means that minimal amounts are present when examined with the unaided eye but that do not clearly show on photographs, "yes" and "+" mean dye is clearly visible, and "++" means heavy dye presence.

Table 1 shows the results for a control mouse treated with 10 μl of phosphate buffer solution (PBS) and no dye.

Table 2 shows the results for dye administered in various concentrations in a single dose with heavy anesthesia.

Table 3 shows the results for dye administered in various concentrations in a single dose with moderate anesthesia.

Table 4 shows the results for dye administered in a supine position at various concentrations in a single dose with heavy anesthesia.

Table 5 shows the results for dye administered in various concentrations in a single dose to alert animals.

Table 6 shows the results for dye administered at 30 μl concentration in a single dose to alert animals.

Table 7 shows the results for dye administered dropwise at 30 μl and 50 μl concentrations under heavy and moderate anesthesia.

Table 8 shows the results for dye administered in 5 μl and 2 μl increments showing reduced dye in the stomach at lower incremental doses than larger incremental doses and less the same summed quantity supplied in a single dose. Table 3 shows the results for dye administered in various concentrations in a single dose with moderate anesthesia.

Table 9 shows optimal divided dose conditions for the mouse where essentially no dye reached the stomach and very little dye reached the esophagus.

TABLE 1

Control

| Mouse # | Dye Volume | Position At Delivery | Position Post Delivery | Anesthesia | Time To Sacrifice | Nose Skin | Nasal Cavity | Oral Cavity | Larynx | Esophagus Upper/Lower | Stomach | Intestine | Trachea Upper/Lower | Lung | Notes |
|---|---|---|---|---|---|---|---|---|---|---|---|---|---|---|---|
| 1 | 0 μl (10 μl of PBS) | N/A | N/A | N/A | N/A | − | − | − | − | −/− | − | − | −/− | − | Control mouse; 10 μl of PBS total. |

TABLE 2

Dye Test, 200 μl of anesthesia (heavy)

| Mouse # | Dye Volume | Position At Delivery | Position After Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|
| 2 | 10 μl | Upright | Not held | 200 μl (heavy) | 60 min | Yes | Yes | Yes | Yes | Traces/Traces |
| 3 | 10 μl | Upright | Not held | 200 μl (heavy) | 60 min | Yes | Yes | Yes | Yes | Yes/Yes |
| 4 | 20 μl | Upright | Not held | 200 μl (heavy) | 60 min | Yes | Yes | Yes | Yes | Yes/Yes |
| 5 | 20 μl | Upright | Not held | 200 μl (heavy) | 60 min | Yes | Yes | Yes | Yes | Yes/Yes |
| 6 | 30 μl | Upright | Not held | 200 μl (heavy) | 60 min | Yes | Yes | Yes | Yes | Yes/Yes |
| 7 | 30 μl | Upright | Not held | 200 μl (heavy) | 60 min | Yes | Yes | Yes | Yes | Yes/Yes |
| 8 | 40 μl | Upright | Not held | 200 μl (heavy) | 60 min | Yes | Yes | Yes | Yes | Yes/Yes |
| 9 | 50 μl | Upright | Not held | 200 μl (heavy) | 60 min | Yes | Yes | Yes | Yes | Yes/Yes |
| 10 | 50 μl | Upright | Not held | 200 μl (heavy) | 60 min | Yes | Yes | Yes | Yes | Yes/Yes |

| Mouse # | Stomach | Intestine | Trachea Upper/Lower | Lung | Notes |
|---|---|---|---|---|---|
| 2 | Traces | − | −/− | − | Dye did not travel far |
| 3 | + | − | Traces/Traces | − | Traces of dye were seen in the |

TABLE 2-continued

Dye Test, 200 μl of anesthesia (heavy)

| | | | | | |
|---|---|---|---|---|---|
| | | | | | bronchial tubes and also appeared in the stomach |
| 4 | + | – | –/– | – | Dye appeared in stomach |
| 5 | + | – | –/– | – | Dye appeared in stomach |
| 6 | + | – | Yes/Yes | +Left Lung only | Dye was present in the stomach and left lung |
| 7 | – | – | Yes/Yes | + | Dye was throughout esophagus and stopped just before entering the stomach. Dye was mostly in the lungs |
| 8 | + | Yes | Yes/Yes | + Right Lung | There was a slight presence of dye in the right lung and none in the left lung |
| 9 | + | – | Yes/Yes | + | Dye was prominent in all examined areas except intestine |
| 10 | + | – | Yes/Yes | ++ | See above |

TABLE 3

Dye Test, 120 μl of anesthesia (moderate)

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|
| 11 | 30 μl | Upright | Not held | 120 μl (Mod) | 60 min | Yes | Yes | Yes | Yes | Yes/Yes |
| 12 | 30 μl | Upright | Not held | 120 μl (Mod) | 60 min | Yes | Yes | Yes | Yes | Yes/Yes |
| 13 | 50 μl | Upright | Not held | 120 μl (Mod) | 60 min | Yes | Yes | Yes | Yes | Yes/Yes |
| 14 | 50 μl | Upright | Not held | 120 μl (Mod) | 60 min | Yes | Yes | Yes | Yes | Yes/Yes |

| Mouse # | Stomach | Intestine | Trachea Upper/Lower | Lung | Notes |
|---|---|---|---|---|---|
| 11 | ++ | – | Yes/Yes | Traces | Traces of dye in the lungs, and heavy in the stomach |
| 12 | + | – | Yes/Yes | Traces | Less presence of the dye in the stomach than #11 |
| 13 | ++ | – | Yes/Yes | Traces | Traces of dye in the lungs and heavy in the stomach |
| 14 | ++ | Yes | Yes/Traces | – | Traces seen in esophagus and trachea. Heavy in the stomach. |

TABLE 4

Dye Test; Supine/Supine

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|
| 15 | 10 μl | Supine | Supine | 200 μl (heavy) | 60 min | Yes | Yes | – | Yes | –/– |

TABLE 4-continued

Dye Test; Supine/Supine

| | | | | | | | | | | |
|---|---|---|---|---|---|---|---|---|---|---|
| 16 | 20 µl | Supine | Supine | 200 µl (heavy) | 60 min | Yes | Yes | Yes | Yes | Traces/– |
| 17 | 30 µl | Supine | Supine | 200 µl (heavy) | 60 min | Yes | Yes | Yes | Yes | Yes/Yes |
| 18 | 30 µl | Supine | Supine | 200 µl (heavy) | 60 min | Yes | Yes | Yes | Yes | Yes/Yes |

| Mouse # | Stomach | Intestine | Trachea Upper/Lower | Lung | Notes |
|---|---|---|---|---|---|
| 15 | – | – | –/– | – | |
| 16 | – | – | Traces/Traces | – | Dark spot in lungs was blood |
| 17 | + | – | Yes/Yes | – | Oral delivery |
| 18 | – | – | Yes/Yes | – | Dye was present in the esophagus |

TABLE 5

Varying Dye Volume; Alert Animals

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|
| 19 | 10 µl | Upright | Not held | 0 µl (Alert) | 60 min | – | Yes | Yes | Yes | –/– |
| 20 | 10 µl | Upright | Not held | 0 µl (Alert) | 60 min | – | Yes | Yes | Yes | –/– |
| 21 | 30 µl | Upright | Not held | 0 µl (Alert) | 60 min | Yes | Yes | Yes | Yes | –/– |
| 22 | 30 µl | Upright | Not held | 0 µl (Alert) | 60 min | Yes | Yes | Yes | Yes | –/– |
| 23 | 50 µl | Upright | Not held | 0 µl (Alert) | 60 min | Yes | Yes | Yes | Yes | Traces/Traces |
| 24 | 50 µl | Uprigbt | Not held | 0 µl (Alert) | 60 min | Yes | Yes | Yes | Yes | –/– |

| Mouse # | Stomach | Intestine | Trachea Upper/Lower | Lung | Notes |
|---|---|---|---|---|---|
| 19 | + | Yes | –/– | – | Relative to other mice this mouse did not struggle much during delivery into first nare but slightly struggled during delivery into second nare. |
| 20 | Traces | Yes | –/– | – | See above. |
| 21 | ++ | Yes | –/– | – | There was a great deal of gurgling and coughing of dye. A lot of dye appeared immediately in the mouth upon delivery. |
| 22 | + | Yes | –/– | – | See above. |
| 23 | ++ | Yes | –/– | – | Mouse sneezed and spit up dye into mouth from nasal cavity. It was very difficult to administer all 50 µl. |
| 24 | + | Yes | –/– | Traces | See above. Dye was present in traces in bronchii. |

TABLE 6

Prone Position During Administration; Alert Animals

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|

TABLE 6-continued

Prone Position During Administration; Alert Animals

| 25 | 30 μl | Prone | Not held | 0 μl (Alert) | 60 min | – | Yes | Traces | Traces | 4– |
| 26 | 30 μl | Prone | Not held | 0 μl (Alert) | 60 min | – | Yes | Traces | Traces | –/– |

| Mouse # | Stomach | Intestine | Trachea Upper/Lower | Lung | Notes |
|---|---|---|---|---|---|
| 25 | + | Yes | –/– | – | Dye almost completely moved into the intestine. |
| 26 | ++ | Yes | –/– | – | Dye moved through tbe esophagus completely and was in the stomach. |

TABLE 7

Drop–Wise Administration of Dye

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|
| 27 | 30 μl 1 drop/5 sec interval | Upright | Not held | 200 μl (heavy) | 60 min | Yes | Yes | Yes | Yes | Yes/Yes |
| 28 | 50 μl; 5 μl/nare at 30 sec interval | Upright | Not held | 120 μl (Mod) | 60 min | Yes | Yes | Yes | Yes | Yes/Yes |

| Mouse # | Stomach | Intestine | Trachea Upper/Lower | Lung | Notes |
|---|---|---|---|---|---|
| 27 | + | – | –/– | – | Drops were released and inhaled slowly pausing for five seconds in between. All dye moved down esophagus and into stomach |
| 28 | + | – | –/– | – | Drops were released and inhaled, slowly paused for 30 seconds in between. All dye moved down esophagus into stomach. Animal was not fully asleep. |

TABLE 8

20–40 μl of Dye, Divided Doses (different intervals), 200 μl of anesthesia (heavy*), Supine/Supine

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/Lower |
|---|---|---|---|---|---|---|---|---|---|---|
| 29 | 30 μl; 5 μl/nare at 10 min interval | Supine | Supine | 200 μl (heavy) | 60 min | Yes | Yes | – | Yes | Yes/Yes |
| 30 | 30 μl; 5 μl/nare at | Supine | Supine | 200 μl (heavy) | 60 min | Yes | Yes | Yes | Yes | Yes/Yes |

TABLE 8-continued

20–40 µl of Dye, Divided Doses (different intervals), 200 µl of anesthesia (heavy*), Supine/Supine

| | | | | | | | | | | |
|---|---|---|---|---|---|---|---|---|---|---|
| 31 | 10 min interval 20 µl; 2 µl/ nare at t = 0, 2, 7, 9 and 11 min | Supine | Supine | 200 µl (heavy) | 60 min | Yes | Yes | – | Yes | –/– |
| 32 | 20 µl; 2 µl nare at 2 min interval | Supine | Supine | 200 µl (heavy) | 60 min | Yes | Yes | Yes | Yes | Yes/Yes |
| 33 | 20 µl; 2 µl/ nare at 5 min interval | Supine | Supine | 200 µl (heavy) | 60 min | Yes | Yes | Yes | Yes | Yes/– |
| 34 | 40 µl; 2 µl/ nare at 5 min interval | Supine | Supine | 200 µl (heavy) | 60 min | Yes | Yes | Yes | Yes | Yes/Yes |
| 35 | 30 µl; 2 µl/ nare at 5 min interval | Supine | Supine | 200 µl (Mod*) | 60 min | Yes | Yes | Yes | Yes | Yes/Yes |
| 36 | 30µl; 2 µl/ nare at5 min interval | Supine | Supine | 200 µl (Mod*) | 60 min | Yes | Yes | Yes | Yes | Yes/Yes |

| Mouse # | Stomach | Intestine | Trachea Upper/ Lower | Lung | Notes |
|---|---|---|---|---|---|
| 29 | + | – | Yes/Yes | + | |
| 30 | + | – | Yes/Yes | Traces | |
| 31 | – | – | –/– | – | The 5 min interval between t = 2 and t = 7 min favored in maintenance |
| 32 | + | – | –/– | – | |
| 33 | – | – | –/– | – | |
| 34 | +/+ | – | –/– | – | Mouse started to wake after about 32 µl were administered. |
| 35 | + | – | –/– | – | Mouse was NOT heavily anesthetized like others given the same amount of anesthesia. It began to wake and move after being given 16 µl of dye. |
| 36 | + | – | –/– | – | See above |

*Some mice, even when given 200 µl of Ketamine/Xylazine could not be considered heavily anesthetized because they behaved like moderately anesthetized animals.

TABLE 9

Optimal Conditions for Intranasal Delivery and Maintenance

| Mouse # | Dye Volume | Position At Delivery | Position Post Delivery | Anesthesia Dose/Level | Time To Sacrifice | Nose Skin | Nasal Cavity | Oral Cavity | Larynx | Esophagus Upper/ Lower |
|---|---|---|---|---|---|---|---|---|---|---|
| 37 | 30 µl; 2 µl/ nare at 5 min interval | Supine | Supine | 200 µl (heavy) | 60 min | Yes | Yes | Yes | Yes | Traces/– |

TABLE 9-continued

Optimal Conditions for Intranasal Delivery and Maintenance

| | | | | | | | | | | | |
|---|---|---|---|---|---|---|---|---|---|---|---|
| 38 | 30 µl; 2 µl/nare at 5 min interval | Supine | Supine | 400 µl (heavy) | 60 min | Yes | Yes | Yes | Yes | –/– | |
| 39 | 30 µl; 2 µl/nare at 5 min interval | Supine | Supine | 350 µl (heavy) | 60 min | Yes | Yes | Yes | Yes | Traces/– | |

| Mouse # | Stomach | Intestine | Trachea Upper/Lower | Lung | Notes |
|---|---|---|---|---|---|
| 37 | – | – | –/– | – | A small isolated patch was found halfway down esophagus. No dye was in stomach, trachea or lungs. The dark spots on the lungs are blood clots. |
| 38 | – | – | –/– | – | Animal needed additional anesthetic during dye administration in order to stay heavily anesthetized until dye was completely administered. |
| 39 | – | – | Traces/– | – | Animal needed additional anesthetic during dye administration in order to stay heavily anesthetizced until dye was completely administered. |

What is claimed is:

1. A method for nasal application of a medicinal substance which comprises applying the substance through the nose in a maximum amount that is insufficient to immediately stimulate an excretory response that would clear a significant portion of the substance from nasal and sinus passages and within a time period of less than one hour, repeating the application of the substance, through the nose in a maximum amount that is insufficient to immediately stimulate an excretory response that would clear a significant portion of the substance from nasal and sinus passages, at least once and at a minimum a sufficient number of times to provide an effective total dose of the substance.

2. The method of claim 1 where the application is repeated a sufficient number of times within the hour to maximize the total dose without stimulating an excretory response that would clear a significant portion of the substance from nasal and sinus passages.

3. The method of claim 1 where the substance is a nasally absorbable medicine.

4. The method of claim 1 where the substance is a nasally active medicine.

5. The method of claim 1 where the substance is selected from the group consisting of vaccines, antigens, epitopes, adjuvants, viral vectors, bacterial vectors, immune modulators, delivery vehicles, and drugs including antibiotics, hormones, antibodies, anti-inflammatories, antipyretics, antispasmotics, anesthetics, chemotherapeutic agents, sedatives, analgesics, vasodialators, and vasoconstrictors.

6. The method of claim 1 where the number of applications is from 3 to about 15 applications within the hour.

7. The method of claim 1 where the mammal is a supine mouse.

8. The method of claim 1 where the mammal is a prone chinchilla.

9. The method of claim 1 where the mammal is a human.

10. The method of claim 1 where the medical substance is a vaccine.

11. The method of claim 10 where the vaccine is a vaccine for non-typeable *haemophilus influenzae*.

12. The method of claim 11 where the vaccine contains an epitope of P6 protein of *haemophilus influenzae*.

13. The method of claim 11 where the vaccine contains an epitope of P5 protein of *haemophilus influenzae*.

14. The method of claim 11 where the vaccine is a vaccine against hepatitis B.

* * * * *